United States Patent [19]

Tomcufcik et al.

[11] 4,261,896

[45] Apr. 14, 1981

[54] 1-SUBSTITUTED-2-(SUBSTITUTED-IMINO)-1H-1,2-DIHYDROBENZ[CD]INDOLES

[75] Inventors: Andrew S. Tomcufcik, Old Tappan; Raymond G. Wilkinson, Montvale, both of N.J.

[73] Assignee: American Cyanamid Company, Stamford, Conn.

[21] Appl. No.: 97,085

[22] Filed: Nov. 23, 1979

[51] Int. Cl.³ ............................................. C07D 209/90
[52] U.S. Cl. ........................... 260/326.9; 260/326.85; 424/263; 424/267; 424/274; 546/200; 546/272
[58] Field of Search .......................... 260/326.9, 326.85

[56] References Cited

U.S. PATENT DOCUMENTS

| | | | |
|---|---|---|---|
| 3,649,645 | 3/1972 | Yamada et al. | 260/326.9 |
| 4,146,541 | 3/1979 | Schwander et al. | 260/326.9 |

OTHER PUBLICATIONS

Chem. Abs., vol. 73:57175x, (1970) (Fr. Demande 2,005,697).
Yamada et al., Chem. Abs., vol. 75:119198j, (1971).
Brack et al., Chem. Abs., vol. 63:15021f-g, (1965) (Fr. 1,388,599).

*Primary Examiner*—Mary C. Lee
*Attorney, Agent, or Firm*—Edward A. Conroy, Jr.

[57] ABSTRACT

Novel 1-substituted-2-(substitutedimino)-1H-1,2-dihydrobenz[cd]indoles useful as inhibitors of platelet aggregation.

14 Claims, No Drawings

1-SUBSTITUTED-2-(SUBSTITUTED-IMINO)-1H-1,2-DIHYDROBENZ[CD]INDOLES

DESCRIPTION OF THE INVENTION

This invention is concerned with compounds of the formula:

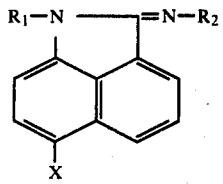

wherein $R_1$ is selected from the group comprising lower alkyl ($C_1$-$C_4$), substituted benzyl and

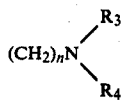

wherein n is an integer 2 or 3 and $R_3$ and $R_4$ are the same or different and are selected from the group comprising lower alkyl ($C_1$-$C_4$); $R_2$ is selected from the group comprising butyl, phenyl,

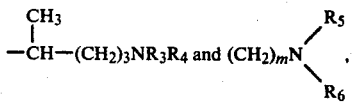

wherein m is an integer 2 or 3 and $R_5$ and $R_6$ are the same or different and are selected from the group comprising lower alkyl ($C_1$-$C_4$), hydrogen and

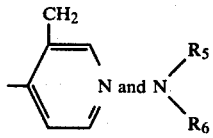

taken together may be

X is selected from the group comprising hydrogen and halogen, together with the pharmaceutically acceptable salts thereof.

The compounds of the present invention may be prepared according to the following flowchart.

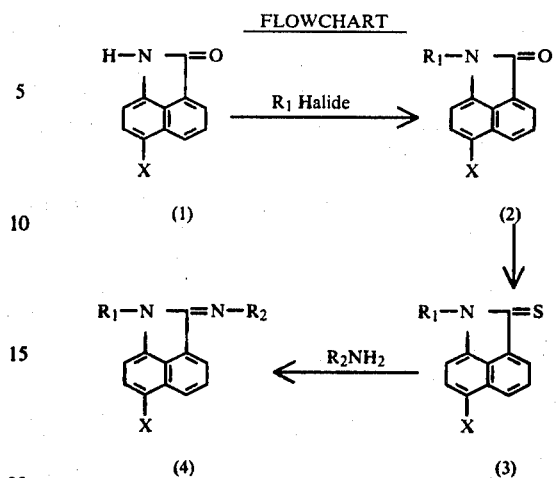

FLOWCHART

A substituted benz[cd]indol-2(1H)-one (1) is dissolved in a solvent such as dimethylformamide, treated portionwise with sodium hydride in mineral oil and then with an $R_1$ halide, heated, cooled, diluted with water, acidified and filtered. The filtrate is extracted with chloroform. The aqueous portion is made basic, extracted with chloroform and the chloroform evaporated giving 1-substituted benz[cd]indol-2-(1H)-ones (2) where $R_1$ and X are as described above. The compound (2) is dissolved in a solvent such as dioxane and refluxed with phosphorous pentasulfide. The solvent is evaporated, the residue is triturated with a base and extracted with chloroform. The solvent is evaporated giving 1-substituted benz[cd]indol-2(1H)-thiones (3), where $R_1$ and X are as described above. The above thione (3) and the appropriate $R_2$ amine (ie. N,N-dimethyl-1,3-propanediamine, N',N',4-trimethyl-1,4-butanediamine, N-(3-aminopropyl)piperidine, etc.) in dioxane is treated with mercuric acetate and refluxed. The mixture is filtered and the filtrate evaporated. The residue is dissolved in water, acidified, clarified and the filtrate made basic and extracted with chloroform. The chloroform is evaporated and the residue is dissolved in a 4:1 mixture of benzene and chloroform and chromatographed giving the base of products (4), where $R_1$, $R_2$ and X are as described above. These bases may be converted to their pharmaceutically acceptable salts by conventional procedures.

The aggregation of blood platelets is an important mechanism in thrombosis and as the degree of aggregation increases the tendency of thrombus formation also increases. The compounds of the present invention inhibit the aggregation of blood platelets and thus are useful as antithrombotic agents in the treatment of well known thrombotic conditions resulting from platelet aggregation. Such conditions include, for example, arterial thrombosis, pulmonary embolism, cerebrovascular disease, rheumatic heart disease, myocardial infarction, thrombophlebitis or thromboembolic conditions which may develop spontaneously following surgery, trauma or disease processes such as coronary occlusion and congestive heart failure. They may also be useful in reducing transient ischemic attacks of the brain and possibly the heart, as well as extrinsically in preventing the clotting of shed and/or stored blood.

The compounds were tested essentially according to the method of G. V. R. Born, Nature, No. 4832, 927–929 (1962) and J. R. O'Brien, J. Clin. Path., 15, 446–452 (1962). Various concentrations of the test compounds were added in vitro to human platelet rich plasma. Collagen (final concentration 500 mcg./ml.), adenosine diphosphate (final concentration 1 to 4 $\times 10^{-6}$M) or sodium arachidonate (final concentration 0.5 mM to 1.0 mM) was added to induce platelet aggregation. Inhibition of platelet aggregation was determined by measuring the change in the optical density of the platelet rich plasma as compared to control plasma. Test compounds showing inhibition at final concentrations of 25 mcg./ml. or less are considered active.

Table I records the results of this test with representative compounds of this invention.

TABLE I

| Compound | Result |
|---|---|
| 1-(2-Dimethylaminoethyl)-2-(3-dimethyl-aminopropylimino)-1,2-dihydrobenz[cd]-indole trihydrochloride | Active |
| 1-(2-Diethylaminoethyl)-2-(3-dimethyl-aminopropylimino)-1,2-dihydrobenz[cd]-indole trifumarate | Active |
| 1-(2-Diethylaminoethyl)-2-(4-diethyl-amino-2-methylbutyl)-1,2-dihydrobenz-[cd]indole dihydrochloride | Active |
| 1-(3-Dimethylaminopropyl)-2-(3-N-piperi-dinopropylimino)-1,2-dihydrobenz[cd]-indole trioxalate | Active |
| 1-(3-Dimethylaminopropyl)-2-(3-methyl-aminopropylimino)-1,2-dihydrobenz[cd]-indole trihydrochloride | Active |
| 1-(3-Dimethylaminopropyl)-2-(3-isopro-pylaminopropylimino)-1,2-dihydrobenz-[cd]indole trihydrochloride | Active |
| 1-(3-Dimethylaminopropyl)-2-(3-diethyl-aminopropylimino)-1,2-dihydrobenz[cd]-indole dihydrochloride | Active |
| 1-(3-Dimethylaminopropyl)-2-[3-di-(n-Butyl)aminopropylimino]-1,2-dihydro-benz[cd]indole trihydrochloride | Active |
| 1-(3-Dimethylaminopropyl)-2-(3-pyridyl-methylimino)-1,2-dihydrobenz[cd]indole trihydrochloride | Active |
| 1-(3-Diethylaminopropyl)-2-(3-dimethyl-aminopropylimino)-1,2-dihydrobenz[cd]-indole trihydrochloride | Active |
| 1-(4-Chlorobenzyl)-2-(3-dimethyl-aminopropylimino)-1,2-dihydrobenz[cd]-indole dihydrochloride | Active |
| 2-(n-Butylimino)-1-methyl-1,2-dihydro-benz[cd]indole hydrochloride | Active |
| 1-Methyl-2-phenylimino-1,2-dihydrobenz-[cd]indole hydrochloride | Active |
| 6-Bromo-1-(3-dimethylaminopropyl)-2-(3-dimethylaminopropylimino)-1,2-dihydro-benz[cd]indole trihydrochloride | Active |
| 6-Bromo-1-(3-diethylaminopropyl)-2-(3-dimethylaminopropylimino)-1,2-dihydro-benz[cd]indole trihydrochloride | Active |

In a second test, in vivo activity of the compounds as platelet aggregation inhibitors was established. In this test the compounds were administered orally to male rats at doses ranging from 0.1 mg./kg. to 100 mg./kg. of body weight. After an interval of 1 to 2 hours or more the rats were bled and platelet rich plasma obtained. Collagen (final concentration 500 mcg./ml.) or adenosine diphosphate (final concentration 1 to 4$\times 10^{-6}$ M) was added to induce platelet aggregation and comparisons were made between control and treated samples. A compound is considered active if it inhibits aggregation by 30% or more at a dose of 1 to 10 mg./kg. of body weight.

Table II records the results of this test with representative compounds of this invention.

TABLE II

| Compound | Result |
|---|---|
| 1-(2-Dimethylaminoethyl)-2-(3-dimethyl-aminopropylimino)-1,2-dihydrobenz[cd]-indole trihydrochloride | Active |
| 1-(2-Diethylaminoethyl)-2-(3-dimethyl-aminopropylimino)-1,2-dihydrobenz[cd]-indole trifumarate | Active |
| 1-(2-Diethylaminoethyl)-2-(4-diethyl-amino-2-methylbutyl)-1,2-dihydrobenz-[cd]indole dihydrochloride | Active |
| 1-(3-Dimethylaminopropyl)-2-(3-N-piperi-dinopropylimino)-1,2-dihydrobenz[cd]-indole trioxalate | Active |
| 1-(3-Dimethylaminopropyl)-2-(3-methyl-aminopropylimino)-1,2-dihydrobenz[cd]-indole trihydrochloride | Active |
| 1-(3-Dimethylaminopropyl)-2-(3-isopro-pylaminopropylimino)-1,2-dihydrobenz-[cd]indole trihydrochloride | Active |
| 1-(3-Dimethylaminopropyl)-2-(3-diethyl-aminopropylimino)-1,2-dihydrobenz[cd]-indole dihydrochloride | Active |
| 1-(3-Dimethylaminopropyl)-2-[3-di-(n-butyl)aminopropylimino]-1,2-dihydro-benz[cd]indole trihydrochloride | Active |
| 1-(3-Dimethylaminopropyl)-2-(3-pyridyl-methylimino)-1,2-dihydrobenz[cd]indole trihydrochloride | Active |
| 1-(3-Diethylaminopropyl)-2-(3-dimethyl-aminopropylimino)-1,2-dihydrobenz[cd]-indole trihydrochloride | Active |
| 1-(4-Chlorobenzyl)-2-(3-dimethyl-aminopropylimino)-1,2-dihydrobenz[cd]-indole dihydrochloride | Active |
| 2-(n-Butylimino)-1-methyl-1,2-dihydro-benz[cd]indole hydrochloride | Active |
| 1-Methyl-2-phenylimino-1,2-dihydrobenz-[cd]indole hydrochloride | Active |
| 6-Bromo-1-(3-dimethylaminopropyl)-2-(3-dimethylaminopropylimino)-1,2-dihydro-benz[cd]indole trihydrochloride | Active |
| 6-Bromo-1-(3-diethylaminopropyl)-2-(3-dimethylaminopropylimino)-1,2-dihydro-benz[cd]indole trihydrochloride | Active |
| 6-Chloro-2-(4-diethylamino-2-methyl-butylimino)-1-methyl-1,2-dihydrobenz-[cd]indole difumarate | Active |

In a third test, the in vivo platelet aggregation inhibition activity of the test compound was determined in a mouse. The ability of a compound to inhibit the respiratory depression associated with platelet aggregation and thrombosis produced by intravenous administration of arachidonic acid was determined. Mice were treated orally by gastric gavage with the test compound in a starch suspension at doses ranging from 0.1 mg./kg. to 100 mg./kg. of body weight. One to 2 hours (or more) later a challenge dose of arachidonic acid was given to the mice intravenously at a concentration of 50 mg./kg. The duration of resipratory distress for each animal was recorded by observation and compared to controls who received only arachidonic acid and starch vehicle. A compound is considered active if it reduces the duration of respiratory distress by 30% or more at doses of 1 to 10 mg./kg. of body weight. The results of this test on representative compounds of this invention appear in Table III.

TABLE III

| Compound | Result |
|---|---|
| 1-(2-Dimethylaminoethyl)-2-(3-dimethyl-aminopropylimino)-1,2-dihydrobenz[cd]-indole trihydrochloride | Active |
| 1-(2-Diethylaminoethyl)-2-(3-dimethyl-aminopropylimino)-1,2-dihydrobenz[cd]- | Active |

TABLE III-continued

| Compound | Result |
| --- | --- |
| indole trifumarate | |
| 1-(2-Diethylaminoethyl)-2-(4-diethyl-amino-2-methylbutyl)-1,2-dihydrobenz-[cd]indole dihydrochloride | Active |
| 1-(3-Dimethylaminopropyl)-2-(3-N-piperi-dinopropylimino)-1,2-dihydrobenz[cd]-indole trioxalate | Active |
| 1-(3-Dimethylaminopropyl)-2-(3-methyl-aminopropylimino)-1,2-dihydrobenz[cd]-indole trihydrochloride | Active |
| 1-(3-Dimethylaminopropyl)-2-(3-isopro-pylaminopropylimino)-1,2-dihydrobenz-[cd]indole trihydrochloride | Active |
| 1-(4-Chlorobenzyl)-2-(3-dimethyl-aminopropylimino)-1,2-dihydrobenz[cd]-indole dihydrochloride | Active |
| 2-(n-Butylimino)-1-methyl-1,2-dihydro-benz[cd]indole hydrochloride | Active |
| 6-Bromo-1-(3-diethylaminopropyl)-2-(3-dimethylaminopropylimino)-1,2-dihydro-benz[cd]indole trihydrochloride | Active |

EXAMPLE 1

Preparation of 1-substituted benz [cd]indol-2(1H)-ones

The 1-substituted benz [cd]indol-2(1H)-ones of this invention are prepared as exemplified by the following procedure for the synthesis of 1-(2-dimethylaminoethyl)benz[cd]-2(1H)-one (I).

Six grams of dried benz [cd]indol-2(1H)-one is dissolved in 75 ml. of dry dimethylformamide and the solution stirred as 3.6 g. of 50% sodium hydride (in mineral oil) is added in small portions. When addition is complete and gas evolution has ceased, 5.1 g. of 2-dimethylaminoethyl chloride hydrochloride is added, and the reaction mixture is warmed slowly to 95°–100° C. and held at this temperature for 30 minutes. It is then cooled to room temperature and 5 ml. of ethanol is added to destroy any unused sodium hydride. The reaction mixture is diluted with 2 volumes of cold water, made acid (pH 2) with concentration hydrochloric acid, and then clarified by filtration through diatomaceous earth. The aqueous filtrate is extracted with two portions of chloroform (equal in volume to the aqueous solution). The aqueous solution is then made basic (pH 12) with 10N sodium hydroxide. The mixture is extracted with 2 portions of chloroform (equal in volume to the aqueous solution). The chloroform extracts are combined, dried over magnesium sulfate, and the chloroform is removed in vacuo, leaving 10.0 g. of 1-(2-dimethylaminoethyl) benz[cd]-2(1H)-one (I) as thin yellow oil. A portion is converted to its hydrochloride salt which melts at 222°–223° C. with decomposition.

The following 1-substituted benz [cd]indol-2(1H)-ones are prepared essentially by the procedure described above.

(Ia) 1-(2-Diethylaminoethyl)benz[cd]indol-2 (1H)-one, HCl salt, mp. 195°–196° C.

(Ib) 1-(3-Diethylaminopropyl)benz[cd]indol-2(1H)-one, HCl salt, mp. 145°–146.5° C.

1-Methylbenz[cd]indol-2 (1H)-one (Ic), mp. 78.5°–79° C. and 1-(3-dimethylaminopropyl)benz [cd]-2(1H)-one (Id), HCl salt, mp. 200°–201.5° C. are described in the chemical literature.

By the procedure described for Compound I, 6-bromobenz[cd]indol-2(1H)-one and 3-diethylaminopropyl chloride hydrochloride yield 6-bromo-1-(3-diethylaminopropylbenz[cd]-indol-2 (1H)-one (Ie), HCl salt, mp. 183°–185° C., while 3-dimethylaminopropyl chloride hydrochloride yields 6bromo-1-(3-dimethylaminopropyl) benz[cd]-2(1H)-one (If), HCl salt, mp. 264°–267° C. Similarly, 6-chlorobenz[cd]indol-2(1H)-one and methyl iodide yield 6-chloro-1-methyl-benz[cd]-2(1H)-one (Ig), while benz[cd]indol-2(1H)-one and 4-chlorobenzyl chloride yield 1-(4-chlorobenzyl)-benz[cd]indol-2(1H)-one (Ih), mp. 128°–129.5° C.

EXAMPLE 2

Preparation of 1-substituted benz[cd]indol-2-thiones

The synthesis of the title compounds is exemplified by the preparation of 1-(2-dimethylaminoethyl)benz[cd]indole-2-thione (IIa). Eleven and five-tenths grams of 1-(2-dimethylaminoethylbenz[cd]indol-2 (1H)-one (Example 1) is dissolved in 100 ml. of dioxane, 6 g. of phosphorous pentasulfide is added and the mixture is then stirred and heated under reflux for 30 minutes. The volatile materials are removed in vacuo, and the residue is triturated with 200 ml. of 2 N sodium hydroxide. The mixture is extracted with two 200 ml. portions of chloroform. The chloroform extracts are combined and dried over magnesium sulfate. Removal of the chloroform leaves 12.2 g. of a thick oily residue of 1-(2-dimethylaminoethyl)-benz[cd]indole-2(1H)-thione, which is used for syntheses without further purification.

The dioxane may be replaced by other suitable solvents such as benzene, toluene, pyridine, 1,2-dimethoxyethane and the like. In a similar manner the following 1-substitutedbenz[cd]indole-2(1H)-thiones are prepared from the corresponding 2-one derivatives of Example 1.

(IIb) 1-(2-Diethylaminoethyl)benz [cd]indole-2(1H)-thione (IIc) 1-(3-Diethylaminopropyl)benz [cd]-indole-2(1H)-thione (IId) 1-Methylbenz[cd]indole-2(1H)-thione, mp. 127.5°–128.5° C.

(IIe) 1-(3-Dimethylaminopropyl)benz[cd]-indole-2 (1H)-thione (IIf) 6-Bromo-1-(3-diethylaminopropyl)-benz[cd]indole-2(1H)-thione (IIg) 6-Bromo-1-(3-dimethylaminopropyl)-benz[cd]indole-2(1H)-thione (IIh) 6-Chloro1-methylbenz[cd]indole-2(1H)-thione (IIi) 1-(4-Chlorobenzyl)benz [cd]indole-2(1H)-thione, mp. 128.5°–130° C.

EXAMPLE 3

1-(2-Dimethylaminoethyl)-2-(3-dimethylamino-propylimino)-1,2-dihydrobenz[cd]indole trihydrochloride A solution of 3.9 g. of 1-(2-dimethylaminoethyl-benz[cd]indole-2(1H)-thione (Example IIa) and 1.8 g. of N,N-dimethyl-1,3-propanediamine in 65 ml. of dioxane is treated with 5.3 g. of mercuric acetate and the mixture stirred and heated under reflux for 30 minutes. The precipitated mercuric sulfide is collected on diatomaceous earth, and the precipitate is washed with hot dioxane until the runnings are water white. The combined dioxane filtrate and washes are concentrated to dryness in vacuo. The residue is dissolved in 50 ml. of water, acidified to pH 2 with concentrated hydrochloric acid, and clarified. The filtrate is made basic (pH 10) with 10N sodium hydroxide, and the mixture is extracted with 200 ml. of chloroform. The chloroform layer is separated, dried over magnesium sulfate, and the chloroform is removed in vacuo. The residue (4.2 g.) is dissolved in a mixture of benzene and chloroform (15 ml. of a 4:1 mixture) and purified by chromatography on an alumina column, eluting with a 2:1 benzene:-chloroform mixture. The main fraction gives 3.8 g. of the base, which, upon treatment with excess ethanolic hydrogen chloride and precipitation with diethyl ether, gives 3.7 g. of the subject compound as yellow crystals, melting at 202°–205° C.

EXAMPLE 4

1-(2-Diethylaminoethyl)-2-(3-dimethylamino-propylimino)-1,2-dihydrobenz[cd]indole trifumarate The preparation of the title compound is carried out essentially by the procedure of Example 3, an equivalent of 1-(2-diethylaminoethyl)benz[cd]indole-2(1H)-thione (Example IIb) replacing the 1-(2-dimethylaminoethyl)benz[cd]indole-2(1H)-thione. The free base is converted to its trifumarate salt, which melts at 148° C.

EXAMPLE 5

1-(2-Diethylaminoethyl)-2-(4-diethylamino-2methyl-butyl)-1,2-dihydrobenz[cd]indole dihydrochloride The preparation of the title compound is carried out essentially by the procedure of Example 3, an equivalent of N',N',4-trimethyl-1,4-butanediamine replacing the N,N-dimethyl-1,3-propanediamine. The free base is converted to its dihydrochloride salt, which melts at 217°–220° C.

EXAMPLE 6

1-(3-Dimethylaminopropyl)-2-(3-N-piperidino-propylimino)-1,2-dihydrobenz[cd]indole trioxalate A mixture consisting of 8.1 g. of 1-(3-dimethylaminopropyl)benz [cd]indole-2(1H)-thione (Example IIe), 6 g. of N-(3-aminopropyl) piperidine, 10 g. of mercuric acetate, and 100 ml. of dioxane is stirred and heated under reflux for 15 minutes. The precipitated mercuric sulfide is collected on diatomaceous earth and washed free of color with hot methanol. The filtrate is concentrated to dryness in vacuo, and the residue is slurried with 50 ml. of water and 10N sodium hydroxide to give a pH of 12. The mixture is extracted with 100 ml. of chloroform, which after drying over magnesium sulfate and concentration to about 25 ml., is placed on an alumina column. Elution of the main band with chloroform gives 13.2 g. of the crude base, after removal of the solvent in vacuo. The base is added to a solution of 8 g. of oxalic acid in 200 ml. of ethanol, yielding the 14 g. of trioxalate salt, melting at about 145° C.

EXAMPLE 7

1-(3-Dimethylaminopropyl)-2-(3-methylamino-propylimino)-1,2-dihydrobenz[cd]indole trihydrochloride The subject compound is prepared essentially by the procedure of Example 6, an equivalent of N-methyl-1,3-propanediamine replacing the N-(3-aminopropyl) piperidine. The free base is converted to its trihydrochloride salt (very hygroscopic) with melts at about 220° C.

EXAMPLE 8

1-(3-Dimethylaminipropyl)-2-(3-isopropylamino-propylimino)-1,2-dihydrobenz[cd]indole trihydrochloride The subject compound is prepared essentially by the procedure of Example 6, an equivalent of N-isopropyl-1,3-propanediamine replacing the N-(3-aminopropyl) piperidine. The free base is converted to its trihydrochloride salt which melts at 258°–267° C. with decomposition.

EXAMPLE 9

1-(3-Dimethylaminopropyl)-2-(3-diethylamino-propylimino)-1,2-dihydrobenz[cd]indole dihydrochloride The subject compound is prepared essentially by the procedure of Example 6, an equivalent of N,N-diethyl-1,3-propanediamine replacing the N-(3-aminopropyl) piperidine. The free base is converted to its dihydrochloride salt which melts at 262°–263° C.

EXAMPLE 10

1-(3-Dimethylaminopropyl)-2-[3di(n-butyl)amino-propylimino]-1,2-dihydrobenz[cd]indole trihydrochloride The subject compound is prepared essentially by the procedure of Example 6, an equivalent of N,N-di(n-butyl)-1,3-propanediamine replacing the N-(3-aminopropyl) piperidine. The free base is converted to its trihydrochloride salt which melts at 196°–198° C.

EXAMPLE 11

1-(3-Dimethylaminopropyl)-2-(3-pyridylmethylimino)-1,2-dihydrobenz[cd]indole trihydrochloride The subject compound is prepared essentially by the procedure of Example 6, an equivalent of 3-aminomethylpyridine replacing the N-(3-aminopropyl)piperidine. The free base gives a trihydrochloride salt which melts at about 172° C.

EXAMPLE 12

1-(3-Diethylaminopropyl)-2-(3-dimethylamino-propylimino)-1,2-dihydrobenz[cd]indole trihydrochloride The title compound is prepared essentially by the procedure of Example 3, an equivalent of 1-(3-diethylaminopropyl)benz [cd]indol-2(1H)-thione (Example IIc) replacing the 1-(2-dimethylamino)benz [cd]indole-2(1H)-thione. The trihydrochloride melts at 240°–250° C. with decomposition.

EXAMPLE 13

1-(4-Chlorohenzyl)-2-(3-dimethylaminopropylimino)-1,2-dihydrobenz[cd]indole dihydrochloride The title compound is prepared by the procedure of Example 12, an equivalent of 1-(4-chlorobenzyl)benz[cd]indole-2(1H)-thione replacing the 1-(3-diethylaminopropyl) benz[cd]-indole-2(1H)-thione. The dihydrochloride melts at 225°–228° C.

EXAMPLE 14

2-(n-Butylimino)-1-methyl-1,2-dihydrobenz[cd]indole hydrochloride

A solution of 13 g. of 1-methylbenz[cd]indole-2-(1H)-thione (Example IId) and 5.5 g. of n-butylamine in 125 ml. of dioxane is treated with 21.5 g. of mercuric acetate. The mixture turns black at once, and the temperature rises to about 90° C. The temperature is held at 75°–80° C. for 20 minutes, then at the boiling point for 15 minutes further. The mercuric sulfide is collected in diatomaceous earth, and the precipitate washed free of color with hot dioxane. The combined filtrate and wash are concentrated to dryness in vacuo. The residue is treated with 50 ml. of water and 10 N sodium hydroxide until a pH of 12 is reached. The mixture is extracted with 100 ml. of chloroform, the chloroform layer is dried over magnesium sulfate, and the chloroform removed in vacuo to give a quantitative yield of the crude free base. Treatment with anhydrous hydrogen chloride in an ethanol-acetone solution gives the yellow hydrochloride, melting at 151.5°–153° C.

EXAMPLE 15

1-Methyl-2-phenylimino-1,2-dihydrobenz[cd]indole hydrochloride

The title compound is prepared essentially by the procedure of Example 14, an equivalent of aniline replacing the n-butylamine. The reaction takes place less readily, and refluxing for one hour is necessary to complete the reaction. The hydrochloride salt, prepared with ethanolic hydrogen chloride, melts at about 207° C.

EXAMPLE 16

6-Bromo-1-(3-dimethylaminopropyl)-2-(3dimethylaminopropylimino)-1,2-dihydrobenz[cd]indole trihydrochloride By the general procedure of Example 3, 6-bromo-1-(3-dimethylaminopropyl)benz[cd]-2(1H)-thione (Example IIg) and N,N-dimethyl-1,3-propanediamine yield the subject compound melting at 278°–286° C. with decomposition.

EXAMPLE 17

6-Bromo-1-(3-diethylaminopropyl)-2-(3-dimethylaminopropylimino)-1,2-dihydrobenz[cd]indole trihydrochloride By the general procedure of Example 3, 6-bromo-1-(3-diethylaminopropyl)benz[cd]indole-2(1H)-thione (Example IIf) and N,N-dimethyl-1,3-propanediamine yield the title compound melting at 275°–280° C. with decomposition.

EXAMPLE 18

6-Chloro-2-(4-diethylamino-2-methylbutylimino)-1-methyl-1,2-dihydrobenz[cd]indole difumarate The subject compound is prepared by the general procedure of Example 3, utilizing 6-chloro-1-methylbenz[cd]indole-2(1H)-thione (Example IIh) and N',N',4-trimethyl-1,4-butanediamine. The difumarate salt is prepared in ethanol-acetone solution and melts at about 90° C.

We claim:

1. A compound selected from the group consisting of those of the formula:

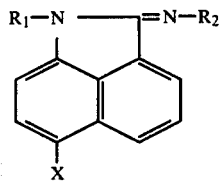

wherein $R_1$ is selected from the group consisting of p-chlorobenzyl and

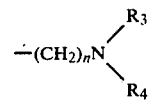

wherein n is the integer 2 or 3 and $R_3$ and $R_4$ are the same or different and are lower alkyl ($C_1$–$C_4$); $R_2$ is selected from the group consisting of butyl,

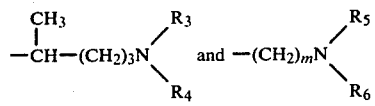

wherein m is the integer 2 or 3 and $R_5$ and $R_6$ are the same or different and are selected from the group consisting of lower alkyl ($C_1$–$C_4$) and hydrogen; X is selected from the group consisting of hydrogen, chloro and bromo; and the pharmaceutically acceptable acid-addition salts thereof.

2. The compound according to claim 1; 1-(2-dimethyl-aminoethyl)-2-(3dimethylaminopropylimino)-1,2-dihydrobenz[cd]indole trihydrochloride.

3. The compound according to claim 1; 1-(2-diethylaminoethyl)-2-(3-dimethylaminopropylimino)-1,2-dihydrobenz[cd]indole trifumarate.

4. The compound according to claim 1; 1(2-diethylaminoethyl)-2-(4-diethylamino-2-methylbutylimino)-1,2-dihydrobenz[cd]indole dihydrochloride.

5. The compound according to claim 1; 1-(3-dimethylaminopropyl)-2-(3-methylaminopropylimino)-1,2-dihydrobenz[cd]indole trihydrochloride.

6. The compound according to claim 1; 1-(3-dimethylaminopropyl)-2-(3-isopropylaminopropylimino)-1,2-dihydrobenz[cd]indole trihydrochloride.

7. The compound according to claim 1; 1-(3-dimethylaminopropyl)-2-(3-diethylaminopropylimino)-1,2,-dihydrobenz[cd]indole dihydrochloride.

8. The compound according to claim 1; 1-(3-dimethylaminopropyl)-2-[3-di(n-butyl)aminopropylimino]-1,2-dihydrobenz[cd]indole trihydrochloride.

9. The compound according to claim 1; 1-(3-diethylaminopropyl)-2-(3-dimethylaminopropylimino)-1,2-dihydrobenz[cd]indole trihydrochloride.

10. The compound according to claim 1; 1-(4-chlorobenzyl)-1-(3-dimethylaminopropylimino)-1,2-dihydrobenz[cd]-indole dihydrochloride.

11. The compound according to claim 1; 1-methyl-2-(n-butylimino)-1,2-dihydrobenz[cd]indole hydrochloride.

12. The compound according to claim 1; 6-bromo-1-(3-dimethylaminopropyl)-2-(3-dimethylaminopropylimino)-1,2-dihydrobenz[cd]indole trihydrochloride.

13. The compound according to claim 1; 6-bromo-1-(3-diethylaminopropyl)-2-(3-dimethylaminopropylimino)-1,2-dihydrobenz[cd]indole trihydrochloride.

14. The compound according to claim 1; 6-chloro-1-methyl-2-(4-diethylamino-2-methylbutylimino)-1,2-dihydrobenz-[cd]indole difumarate.

* * * * *